United States Patent
Indolese et al.

(10) Patent No.: US 6,784,295 B2
(45) Date of Patent: Aug. 31, 2004

(54) COUPLING OF NUCLEOPHILES, VINYL COMPOUNDS OR CO WITH WATER, ALCOHOLS OR AMINES TO ORGANIC COMPOUNDS

(75) Inventors: Adriano Indolese, Möhlin (CH); Anita Schnyder, Allschwil (CH)

(73) Assignee: Solvias AG, Basel (CH)

( * ) Notice: Subject to any disclaimer, the term of this patent is extended or adjusted under 35 U.S.C. 154(b) by 0 days.

(21) Appl. No.: 10/376,224

(22) Filed: Mar. 3, 2003

(65) Prior Publication Data

US 2003/0181688 A1 Sep. 25, 2003

Related U.S. Application Data

(62) Division of application No. 09/799,084, filed on Mar. 6, 2001, now Pat. No. 6,548,684.

(30) Foreign Application Priority Data

| Mar. 6, 2000 | (CH) | ................................................ | 436/00 |
| Mar. 6, 2000 | (CH) | ................................................ | 437/00 |
| Mar. 6, 2000 | (CH) | ................................................ | 438/00 |

(51) Int. Cl.$^7$ ........................ C07B 37/04; C07B 41/12; C07D 217/00
(52) U.S. Cl. ............................................ 546/10; 546/2
(58) Field of Search ........................................ 546/2.1

(56) References Cited

U.S. PATENT DOCUMENTS

5,801,263 A  9/1998 Seitz et al.

OTHER PUBLICATIONS

Albinati et al, Inorganic Chemistry, vol. 26, pp. 503–508, 1987.
Zheng et al., Journal of Organic Chemistry, vol. 63, pp. 9606–9607, 1998.
Littke, et al., "A Convenient and General Method for Pd–Catalyzed Suzuki Cross–Couplings of Aryl Chlorides and Arylboronic Acids", *Angew. Chem Int. Ed.* 1998, *37*, No. 24, pp. 3387–3388.
Pfeffer, "Reactions of cyclopalladated compounds and alkynes: new pathways for organic synthesis?" Recl. Trav. Chim. Pays–Bas 109, 567–576 (1990).
Tsuji, "Synthetic Reactions Based on the Chelation of Heteroatoms," Palladium Reagents and Catalysts, pp. 87–97 (1996), John Wiley & Sons (New York).
Sommovigo, M. and Alper, H. "Aerobic oxidation of ethers and alkenes catalyzed by a novel palladium complex" Journal of Molecular Catalysis, vol. 88 (1994), pp. 151–158.
Ben–David, Y., et al. "Chelate–Assisted, Pd–Catalyzed Efficient Carbonylation of Aryl Chlorides" Journal of the American Chemical Society, vol. 111 (1989), pp. 8742–8744.
Herrmann, W.A., et al. "Palladacycles as Structurally Defined Catalysts for the Heck Olefination of Chloro– and Bromoarenes" Angewandte Chemie. International Edition, vol. 34 (Sep. 15, 1995), pp. 1844–1848.
Hocek, M., et al. "Synthesis and Cytostatic Activity of Substituted 6–Phenylpurine Bases and Nucleosides: Application of the Suzuki–Miyaura Cross–Coupling Reactions of 6–Chloropurine Derivatives with Phenylboronic Acids" Journal of Medicinal Chemistry, vol. 43 (2000), pp.1817–1825.

*Primary Examiner*—Zinna Northington Davis
(74) *Attorney, Agent, or Firm*—Wenderoth, Lind & Ponack, L.L.P.

(57) ABSTRACT

Process for the coupling of
  a) nucleophiles selected from the group alcohols, thioles, amines, metallised hydrocarbons, CH-acidic compounds and metal cyanides, or of
  b) carbon monoxide mixed with water, alcohols, ammonia, primary or secondary amines, to organic compounds selected from the group of leaving-group-containing aromatics, hetero-aromatics with a C-bonded leaving group, aromatic or hetero-aromatic methyl compounds with a leaving group bonded to the methyl group, ethylenically unsaturated organic compounds with a C-bonded leaving group, or organic allyl compounds with a leaving group in allyl position, or
  c) vinyl compounds with leaving-group-containing aromatics, whilst cleaving the leaving group in the presence of Pd complexes with monophospholine ligands as the catalyst, whereby variants b) and c) are carried out in the presence of an inorganic base or organic nitrogen base, the process being characterised in that the Pd complex contains secondary monophosphines with aliphatic, branched or cyclic substituents as ligands.

6 Claims, No Drawings

COUPLING OF NUCLEOPHILES, VINYL COMPOUNDS OR CO WITH WATER, ALCOHOLS OR AMINES TO ORGANIC COMPOUNDS

This application is a Divisional application of Ser. No. 09/799,084, filed Mar. 6, 2001, now U.S. Pat. No. 6,548,684.

The present invention relates to a process for the coupling of a) carbon monoxide together with water, ammonia, alcohols or primary or secondary amines or b) nucleophiles selected from the group of alcohols, thiols, amines, metallised hydrocarbons, CH-acidic compounds and metal cyanides, to organic compounds selected from the group of leaving-group-containing aromatics, hetero-aromatics with a C-bonded leaving group, aromatic or hetero-aromatic methyl compounds with a leaving group bonded to the methyl group, ethylenically unsaturated organic compounds with a C-bonded leaving group, or organic allyl compounds with a leaving group in allyl position, or c) vinyl compounds with leaving-group-containing aromatics, in the presence of Pd-phosphine complexes with ligands from the group of secondary aliphatic monophosphines as catalyst, and optionally in the presence of an inorganic base or organic nitrogen base; the use of Pd-phosphine complexes with secondary aliphatic monophosphines as catalysts for these coupling reactions; new Pd-phosphine complexes; and a composition comprising (a) a Pd(II) salt, a Pd(II) complex salt or a Pd(0) complex and (b) a secondary monophosphine.

It has been known for a long time that Pd-phosphine complexes catalyse the coupling of vinyl compounds, of carbon monoxide mixed with water, ammonia, alcohols or amines, or of nucleophiles, to aromatics, whilst cleaving a leaving group. An overview of this reaction is given in J. Tsuji, Palladium Reagents and Catalysts, John Wiley & Sons, 1996). The phosphine lidands used are primarily tertiary phosphines or ditertiary diphosphines, which are stable in the air and therefore easier to handle. The nucleophile-substituted aromatics are thereby obtainable in good yields and in reasonable reaction times, especially if tertiary phosphines with two to three sterically demanding alkyl groups are used as ligands (see for example A. F. Littke, G. C. Fu, Angew. Chem. Int. Ed. 1998, 37, 3387ff). The preparation of such tertiary phosphines is complex and expensive.

It has now surprisingly been found that for the coupling reaction the secondary monophosphines with sterically demanding aliphatic substituents, which are significantly simpler to produce and are partly available commercially, can be used as ligands for the Pd catalysts. Despite their lower basicity compared to tertiary monophosphines, the catalyst activity is only insignificantly affected and the desired nucleophile-substituted compounds are obtained in high yields.

A first object of the invention is a process for the coupling of a) nucleophiles selected from the group of alcohols, thiols, amines, metallised hydrocarbons, CH-acidic compounds and metal cyanides, or of b) carbon monoxide mixed with water, alcohols, ammonia, primary or secondary amines, to organic compounds selected from the group of leaving-group-containing aromatics, hetero-aromatics with a C-bonded leaving group, aromatic or hetero-aromatic methyl compounds with a leaving group bonded to the methyl group, ethylenically unsaturated organic compounds with a C-bonded leaving group, or organic allyl compounds with a leaving group in allyl position, or c) vinyl compounds with leaving-group-containing aromatics, whilst cleaving the leaving group in the presence of Pd complexes with monophospholine ligands as the catalyst, whereby variants b) and c) are carried out in the presence of an inorganic base or organic nitrogen base, the process being characterised in that the Pd complex contains secondary monophosphines with aliphatic, branched or cyclic substituents as ligands.

The monophosphines used according to the invention may correspond, for example, to formula I, $$HPR_1R_2 \qquad (I),$$

wherein $R_1$ and $R_2$, independently of one another, signify α-branched alkyl or cycloalkyl, or $R_1$ and $R_2$, together with the P-atom, represent a P-heterocycloaliphatic radical with a total of 4 to 8 ring members. $R_1$ and $R_2$ may be substituted or unsubstituted.

$R_1$ and $R_2$ may be unsubstituted or substituted. Suitable substituents are, for example, —OH, —NH$_2$, —NHC$_1$—C$_4$-Alkyl, —N(C$_1$–C$_4$-alkyl)$_2$, —CN, —SO$_3$H, —SO$_3$M, —COOM, —COOH, —COOC$_1$—C$_4$-alkyl, C$_5$–C$_{12}$-cycloalkyl, C$_5$–C$_{12}$-heterocycloalkyl with 1 to 3 hetero atoms selected from the group O, S and N, C$_1$–C$_4$-alkoxy, C$_6$–C$_{12}$-aryl, C$_4$–C$_{11}$-heteroaryl with 1 to 3 hetero atoms selected from the group O, S and N, C$_7$–C$_{12}$-aralkyl, C$_5$–C$_{12}$-heteroaralkyl with 1 to 3 hetero atoms selected from the group O, S and N, C$_7$–C$_{12}$-aralkyl, C$_5$–C$_{12}$-heteroaralkyl with 1 to 3 hetero atoms selected from the group O, S and N, whereby M signifies Li, Na or K. Suitable substituents for the cyclic radicals are also C$_1$–C$_4$-alkyl. Cyclic substituents may be unsubstituted or substituted by halogen (preferably F, Cl or Br), C$_1$–C$_4$-alkyl C$_1$–C$_4$-alkoxy.

$R_1$ and $R_2$ as alkyl may contain for example 3 to 18, preferably 3 to 12, more preferably 3 to 8, and most preferably 3 to 6 carbon atoms. The cycloalkyl may contain for example 3 to 16, preferably 4 to 12, most preferably 5 to 10 ring carbon atoms. The P-heterocycloaliphatic radical preferably contains a total of 5 or 6 ring members.

The α-branched alkyl in question may be alkyl groups whose α-carbon atom is substituted by one to three alkyl radicals. The alkyl radicals preferably contain 1 to 6 carbon atoms, more preferably 1 to 4 carbon atoms and most preferably 1 or 2 carbon atoms. Examples of alkyl radicals are butyl, propyl and preferably ethyl or methyl. A few examples of branched alkyl are isopropyl, iso- and tert.-butyl, 2-methyl-but-2-yl, 2- or 3-pentyl, 2-methyl-hex-2-yl and 2-heptyl.

The cycloalkyl in question may be mono- or polycyclic ring systems. The polycyclic ring systems may consist of, for example, 2 to 4 condensed rings. Examples of cycloalkyl are cyclopropyl, cyclobutyl, cyclopentyl, cyclohexyl, cycloheptyl, cyclooctyl, norbornyl, [2,2,2]-bicyclooctyl, [3,2,1]-bicyclooctyl, [3,2,2]-bicyclononyl, and adamantyl.

The P-heterocycloaliphatic radical in question is preferably radicals in which $R_1$ and $R_2$ in formula I together are tetra- or pentamethylene.

An especially preferred group of secondary monophosphines is the one in which $R_1$ and $R_2$ are selected from the group isopropyl, isobutyl, tert.-butyl, cyclopentyl, cyclohexyl, norbornyl and adamantyl.

Leaving groups are known and are described in literature. Examples of leaving groups are, in particular, halides such as chloride, bromide and iodide, as well as the group R—S(O$_2$)—O—, wherein R is fluorine, alkyl, halogen-alkyl, phenyl, halogen-phenyl, mono-, di- or trimethylphenyl or mono-, di- or tri(halogenmethyl)phenyl. Examples are fluorosulfonyloxy, methylsulfonyloxy, trifluoromethylsulfonyloxy, nonaflate and tosylate. Other known leaving groups are phosphoric acid ester groups of the formula $(RO)_2P(O)O-$. Preferred leaving groups are halides; chloride and bromide are especially preferred. The organic compound may contain one or more leaving groups, for example 1 to 4, preferably one or two leaving groups. At least 0.5 equivalents of nucleophiles are used per leaving group, for example 1 to 5 or 1 to 2 equivalents per leaving group.

The organic compounds with leaving groups that may be mentioned are first of all aromatics. They may also be hydrocarbon aromatics, which contain, for example, 6 to 18 carbon atoms, preferably 6 to 16 carbon atoms, most preferably 6 to 12 carbon atoms.

Examples of hydrocarbon aromatics are benzene, pentalene, indan, indene, indoline, naphthalene, acenaphthylene, anthracene, phenanthrene, fluorene, pyrene, chrysene, naphthacene, diphenyl, diphenylether, diphenylthioether, diphenylmethane and stilbene. Benzene, diphenyl and naphthalene are preferred.

The organic compounds with leaving groups that may be mentioned are also hetero-aromatics. The hetero-aromatics may contain, for example 3 to 16 carbon atoms, preferably 4 to 13 carbon atoms, most preferably 4 to 9 carbon atoms, and at least one hetero atom selected from the group O, S, N and P.

Examples of hetero-aromatics are thiophene, benzothiophene, furan, benzofuran, pyran, chromene, pyrrole, imidazole, pyrazole, pyridine, bipyridyl, pyrazine, pyrimidine, pyridazine, indole, isoindole, 1H-indazole, quinoline, isoquinoline, phthalazine, quinoxaline, quinazoline, carbazole, acridine, phenanthroline, phenazine, thiazole, isothiazole, phenothiazine, oxazole, isooxazole, phenoxazine, pyrazole, piccoline, and lutidine.

The hydrocarbon aromatics and hetero-aromatics may be unsubstituted or substituted by at least one inert substituent, for example 1 to 4 inert substituents. Examples of substituents are $C_1-C_8-$, preferably $C_1-C_4$-alkyl, $C_1-C_8-$, preferably $C_1-C_4$-alkoxy, $C_1-C_8$, preferably $C_1-C_4$-halogenalkyl, $C_1-C_8-$, preferably $C_1-C_4$-hydroxyalkyl, $C_1-C_8-$, preferably $C_1-C_4$-cyanoalkyl, $-CN$, $-NHC_1-C_4$-alkyl, $-N(C_1-C_4$-alkyl$)_2$, $C_1-C_8-$, preferably $C_1-C_4$-alkyl-$NH_2$, $C_1-C_8-$, preferably $C_1-C_4$-alkyl-$NHC_1-C_4$-alkyl, $C_1-C_8-$, preferably $C_1-C_4$-alkyl-$N(C_1-C_4$-alkyl$)_2$, $C_1-C_8-$, preferably $C_1-C_4$-alkyl-X with X equal to $-COOH$, $-COOM$, $-COO-C_1-C_4$-alkyl, $-CO-NH_2-CO-NH-C_1-C_4$aAlkyl, $-CO-N(C_1-C_4$-alkyl$)_2$; benzyl, $-COOH$, $-COOM$, $-CHO$, $-COO-C_1-C_1$-alkyl, $-CO-NH_2$, $-CO-NH-C_1-C_4$-alkyl, $-CO-N(C_1-C_4$-alkyl$)_2$; $C_1-C_8-$ and preferably $C_1-C_4$-alkyl-CO-, $C_6-C_{10}$-aryl-CO$-$, $-NO_2$, $-SO_2-C_1-C_4$-alkyl, $-SO_2-C_1-C_4$-alkoxy, $-SO_3H$, $SO_3M$, $-S-C_1-C_4$-alkyl, whereby M is an alkali metal, for example Li, Na and K.

Examples of alkyl substituents are methyl, ethyl, n- and isopropyl, n-, iso- and tert.-butyl, pentyl, hexyl and octyl. Examples of alkoxy substituents are methoxy, ethoxy, n- and isopropoxy, n-, iso- and tert.-butoxy, pentoxy, hexoxy and octoxy. Examples of halogen-alkyl substituents are fluoromethyl, difluoromethyl, trifluoromethyl, chloromethyl, dichloromethyl, trichloromethyl, perfluoroethyl, chloroethyl, n- and iso-chloro- or fluoropropyl, n-, iso- and tert-chlorobutyl. Examples of hydroxy-alkyl substituents are hydroxymethyl, β-hydroxyethyl, n-hydroxypropyl and n-hydroxybutyl. Examples of cyanoalkyl substituents are cyanomethyl, 2-cyanoeth-1-yl and 3-cyanoprop-1-yl.

The organic compounds with leaving groups may also be aromatic or heteroaromatic methyl compounds with a leaving group bonded to the methyl group (benzylic leaving group). Hetero-aromatics are bonded to the methyl group by a ring carbon atom. Suitable aromatics and hetero-aromatics that are bonded to the methyl group have already been mentioned. The methyl group may be substituted by one or two $C_1-C_8$-alkyl, phenyl or benzyl.

The aromatic or hetero-aromatic methyl compounds may correspond, for example, to formula II,

$$R_a-CR_bR_c-A \qquad (II)$$

wherein

A is a leaving group, $R_a$ signifies unsubstituted or substituted aryl or heteroaryl, and $R_b$ and $R_c$, independently of one another, signify hydrogen, $C_1-C_8$-alkyl, phenyl or benzyl, which are unsubstituted or substituted by $C_1-C_4$-alkyl, $C_1-C_4$-alkoxy, $NHC_1-C_4$-alkyl, $-N(C_1-C_4$-alkyl$)_2$, $-CN$, $-SO_3H$, $-SO_3-C_1-C_4$-alkyl, $-SO_3M$, $-COOM$, $-COOH$, $-COOC_1-C_4$-alkyl, $-COONH_2$, $-COONHC_1-C_4$-alkyl$_2$, $-COON(C_1-C_4$-alkyl$)_2$, $C_5-C_{12}$-cycloalkyl, $C_5-C_{12}$-hetero-cycloalkyl with 1 to 3 hetero atoms selected from the group O, S and N, $C_1-C_4$-alkoxy, $C_6-C_{12}$-aryl, $C_4-C_{11}$-heteroaryl with 1 to 3 hetero atoms selected from the group O, S and N, $C_7-C_{12}$-aralkyl, $C_5-C_{12}$-heteroaralkyl with 1 to 3 hetero atoms selected from the group O, S and N, whereby M signifies Li, Na or K. Cyclic substituents may be unsubstituted or substituted by halogen (preferably F), $C_1-C_4$-alkyl $C_1-C_4$-alkoxy.

In the compounds of formula II, $R_c$ is preferably H and R is preferably hydrogen, or unsubstituted or substituted $C_1-C_6$-alkyl, phenyl or benzyl.

The organic compounds with leaving groups may also be ethylenically unsaturated organic compounds, in which the leaving group is bonded to a vinylic carbon atom. The compounds may be open-chained or cyclic and contain for example 2 to 30, preferably 2 to 20 carbon atoms and optionally hetero atoms selected from the group O, S and N. The compounds may be unsubstituted or may be substituted as defined above for $R_b$. Preferably at least one hydrogen atom is bonded to the carbon atoms of the ethylenically unsaturated group. More preferably, one hydrogen atom is bonded to each carbon atom of the ethylenically unsaturated group. The compounds may correspond, for example, to formula III,

$$R_dR_eC=CR_f-A \qquad (III),$$

wherein

A is a leaving group, $R_d$ and $R_e$, independently of one another, are hydrogen or an open-chained or cyclic hydro-carbon radical or hetero-hydrocarbon radical with hetero atoms, selected from the group O, S and N, which contain 1 to 30, preferably 1 to 20 carbon atoms.

$R_f$ independently has the same significance as $R_d$ and $R_e$; at least one of $R_d$, $R_e$ and $R_f$ signifies a hydrogen atom, $R_d$ and $R_e$, together with the carbon atom to which they are bonded, form a hydrocarbon ring or hetero-hydrocarbon ring with hetero atoms selected from the group O, S and N, with 3 to 12 ring members;

$R_d$ and $R_f$, together with the C=C-group, form a hydrocarbon ring or hetero-hydrocarbon ring with hetero atoms selected from the group O, S and N, with 3 to 12 ring members; and $R_d$, $R_e$, $R_f$ and $R_g$ are unsubstituted or substituted by $C_1$–$C_6$-alkyl, $C_1$–$C_6$-alkoxy, $C_4$–$C_7$-cycloalkyl, $C_6$–$C_{10}$-aryl, $C_7$–$C_{12}$-aralkyl, $C_1$–$C_4$-alkyl-$C_6$–$C_{10}$-aryl, $C_1$–$C_4$-alkoxy-$C_6$–$C_{10}$-aryl, $C_1$–$C_4$-alkyl-$C_7$–$C_{12}$-aralkyl, $C_1$–$C_4$-alkoxy-$C_7$–$C_{12}$-aralkyl, —CO—$OR_5$, —CO—$NR_6R_7$ or —$NR_6R_7$, wherein $R_5$ is H, an alkali metal, $C_1$–$C_6$-alkyl, $C_4$–$C_7$-cycloalkyl, phenyl or benzyl, and $R_6$ and $R_7$, independently of one another, are hydrogen, $C_1$–$C_6$-alkyl, $C_4$–$C_7$-cycloalkyl, phenyl or benzyl, or $R_6$ and $R_7$ together signify tetramethylene, pentamethylene or 3-oxapentylene.

Examples and preferences of substituents have already been mentioned. $R_d$ is preferably a hydrogen atom. Most preferably, $R_d$ and $R_f$ are each a hydrogen atom.

The radicals $R_d$, $R_e$ and $R_f$ may be for example $C_1$–$C_{20}$-alkyl, and preferably $C_1$–$C_{12}$-alkyl, $C_1$–$C_{20}$-heteroalkyl and preferably $C_1$–$C_{12}$-heteroalkyl with hetero atoms selected from the group O, S and N, $C_3$–$C_{12}$-cycloalkyl and preferably $C_4$–$C_8$-cycloalkyl, C-bonded $C_3$–$C_{11}$-heterocycloalkyl and preferably $C_4$–$C_8$-heterocycloalkyl with hetero atoms selected from the group O, S and N, $C_3$–$C_{12}$-cycloalkyl-$C_1$–$C_6$-alkyl and preferably $C_4$–$C_8$-cycloalkyl-$C_1$–$C_6$-alkyl, $C_3$–$C_{11}$-heterocycloalkyl-$C_1$–$C_6$-alkyl and preferably $C_4$–$C_8$-heterocycloalkyl-$C_1$–$C_8$-alkyl with hetero atoms selected from the group O, S and N, $C_6$–$C_{14}$-aryl and preferably $C_6$–$C_{10}$-aryl, $C_5$–$C_{13}$-heteroaryl and preferably $C_5$–$C_9$-heteroaryl with hetero atoms selected from the group O, S and N, $C_7$–$C_{15}$-aralkyl and preferably $C_7$–$C_{11}$-aralkyl, $C_6$–$C_{12}$-hetero-aralkyl and preferably $C_6$–$C_{10}$-heteroaralkyl with hetero atoms selected from the group O, S and N.

If $R_d$ and $R_e$, together with the carbon atom to which they are bonded, or $R_d$ and $R_f$ each together with the C=C-group, form a hydrocarbon ring or hetero-hydrocarbon ring, then the ring preferably contains 4 to 8 ring members. The hetero-hydrocarbon ring may contain for example 1 to 3, preferably one or two hetero atoms.

The organic compounds with leaving groups may also be organic allyl compounds with a leaving group in allyl position. The compounds may be open-chained or cyclic and contain for example 2 to 30, preferably 2 to 20 carbon atoms and optionally hetero atoms selected from the group O, S and N. The compounds may be unsubstituted or may be substituted as defined above for $R_b$. The compounds may correspond, for example, to formula IV, $$R_dR_eC=CR_fCHR_g-A \qquad (IV),$$

wherein

A is a leaving group;

$R_d$ and $R_e$, independently of one another, are hydrogen or an open-chained or cyclic hydro-carbon radical or hetero-hydrocarbon radical with hetero atoms, selected from the group O, S and N, which contain 1 to 30, preferably 1 to 20 carbon atoms.

$R_f$ independently has the same significance as $R_d$ and $R_e$; at least one of $R_d$, $R_e$ and $R_f$ signifies a hydrogen atom;

$R_g$ has the significances of $R_d$;

$R_d$ and $R_e$, together with the carbon atom to which they are bonded, form a hydrocarbon ring or hetero-hydrocarbon ring with hetero atoms selected from the group O, S and N, with 3 to 12 ring members;

$R_d$ and $R_g$, together with the C=C-group, form a hydrocarbon ring or hetero-hydrocarbon ring with hetero atoms selected from the group O, S and N, with 3 to 12 ring members;

$R_d$ and $R_f$, together with the C=C—CH-group, form a hydrocarbon ring or hetero-hydrocarbon ring with hetero atoms selected from the group O, S and N, with 4 to 12 ring members;

and $R_d$, $R_e$, $R_f$ and $R_g$ are unsubstituted or substituted by $C_1$–$C_6$-alkyl, $C_1$–$C_6$-alkoxy, $C_4$–$C_7$-cycloalkyl, $C_6$–$C_{10}$-aryl, $C_7$–$C_{12}$-aralkyl, $C_1$–$C_4$-alkyl-$C_6$–$C_{10}$-aryl, $C_1$–$C_4$-alkoxy-$C_6$–$C_{10}$-aryl, $C_1$–$C_4$-alkyl-$C_7$–$C_{12}$-aralkyl, $C_1$–$C_4$-alkoxy-$C_7$–$C_{12}$-aralkyl, —CO—$OR_5$, —CO—$NR_6$  is H, an alkali metal, $C_1$–$C_6$-alkyl, $C_4$–$C_7$-cycloalkyl, phenyl or benzyl, and $R_6$ and $R_7$, independently of one another, are hydrogen, $C_1$–$C_6$-alkyl, $C_4$–$C_7$-cycloalkyl, phenyl or benzyl, or $R_6$ and $R_7$ together signify tetramethylene, pentamethylene or 3-oxapentylene.

Examples and preferences of substituents have already been mentioned.

The radicals $R_d$, $R_e$, $R_f$ and $R_g$ may be for example $C_1$–$C_{20}$-alkyl, and preferably $C_1$–$C_{12}$-alkyl, $C_1$–$C_{20}$-heteroalkyl and preferably $C_1$–$C_{12}$-heteroalkyl with hetero atoms selected from the group O, S and N, $C_3$–$C_{12}$-cycloalkyl and preferably $C_4$–$C_8$-cycloalkyl, C-bonded $C_3$–$C_{11}$-heterocycloalkyl and preferably $C_4$–$C_8$-heterocycloalkyl with hetero atoms selected from the group O, S and N, $C_3$–$C_{12}$-cycloalkyl-$C_1$–$C_6$-alkyl and preferably $C_4$–$C_8$-cycloalkyl-$C_1$–$C_6$-alkyl, $C_3$–$C_{11}$-heterocycloalkyl-$C_1$–$C_6$-alkyl and preferably $C_4$–$C_8$-heterocycloalkyl-$C_1$–$C_6$-alkyl with hetero atoms selected from the group O, S and N, $C_8$–$C_{14}$-aryl and preferably $C_6$–$C_{10}$-aryl, $C_5$–$C_{13}$-heteroaryl and preferably $C_5$–$C_9$-heteroaryl with hetero atoms selected from the group O, S and N, $C_7$–$C_{15}$-aralkyl and preferably $C_7$–$C_{11}$-aralkyl, $C_6$–$C_{12}$-hetero-aralkyl and preferably $C_6$–$C_{10}$-heteroaralkyl with hetero atoms selected from the group O, S and N.

If $R_d$ and $R_e$ with the carbon atom, or $R_d$ and $R_f$ together with the C=C-group, or $R_d$ and $R_g$ together with the C=C—CH-group, form a hydrocarbon ring or hetero-hydrocarbon ring, then the ring preferably contains 4 to 8 ring members. The hetero-hydrocarbon ring may contain for example 1 to 3, preferably one or two hetero atoms.

Variant a)

The nucleophiles in question are, for example, alcohols and thiols. These may be aliphatic, cycloaliphatic or aromatic alcohols and thiols, which contain 1 to 20, preferably 1 to 12, most preferably 1 to 6 carbon atoms, and are unsubstituted or substituted by $C_1$–$C_4$-halogenalkyl, —N($C_1$–$C_4$-alkyl)$_2$, —CN, —$SO_3H$, —$SO_3M$, —COOM, —COOH, —COO$C_1$–$C_4$-alkyl, $C_5$–$C_{12}$-cycloalkyl, $C_5$–$C_{12}$-heterocycloalkyl with 1 to 3 hetero atoms selected from the group O, S and N, $C_1$–$C_4$-alkoxy, $C_6$–$C_{12}$-aryl, $C_4$–$C_{11}$-heteroaryl with 1 to 3 hetero atoms selected from the group O, S and N, $C_7$–$C_{12}$-aralkyl, $C_5$–$C_{12}$-heteroaralkyl with 1 to 3 hetero atoms selected from the group O, S and N, whereby M signifies Li, Na or K. Suitable substituents for the cyclic radicals are also $C_1$–$C_4$-alkyl. Cyclic substituents may be unsubstituted or substituted by halogen (preferably F), $C_1$–$C_4$-alkyl, $C_1$–$C_4$-halogenalkyl or $C_1$–$C_4$-alkoxy.

Tertiary and aromatic alcohols are preferred.

The nucleophiles in question are, for example, primary and secondary amines. These may be aliphatic, cycloaliphatic or aromatic amines. The secondary amines may be N-heterocycloaliphatic amines. The amines preferably contain 1 to 30, more preferably 1 to 20, most preferably 1 to 12 carbon atoms. The amines may be unsubstituted or substituted by the substituents already defined for alcohols.

The alcohols, thiols and amines may correspond to formula II $$R_3-XH \qquad (V),$$

wherein X is —O—, —S— or —N—$R_4$, $R_4$ is H or independently has the same significance as $R_3$, $R_3$ signifies a monovalent, saturated or unsaturated aliphatic radical with 1 to 12 carbon atoms, a saturated or unsaturated cycloaliphatic radical with 3 to 8 carbon atoms, a saturated or unsaturated heterocycloaliphatic radical with 3 to 8 ring members and one or two hetero atoms from the group O, S, N and NR', a saturated or unsaturated cycloaliphatic-aliphatic radical with 4 to 12 carbon atoms, a saturated or unsaturated heterocycloaliphatic-aliphatic radical with 3 to 12 carbon atoms and one or two hetero atoms from the group O, S, N and NR', an aromatic radical with 6 to 10 carbon atoms, a hetero-aromatic radical with 4 to 9 carbon atoms and one or two hetero atoms from the group O, S and N, an aromatic-aliphatic radical with 7 to 12 carbon atoms or a hetero-aromatic-aliphatic radical with 5 to 11 carbon atoms and one or two hetero atoms from the group O, S and N, whereby R' is $C_1$–$C_8$-alkyl, preferably $C_1$–$C_4$-alkyl, $C_5$- or $C_6$-cycloalkyl, $C_6$–$C_{10}$-aryl such as phenyl or naphthyl, or phenyl or phenylethyl.

or $R_3$ and $R_4$, together with the N-atom, form a 3- to 8-membered heterocyclic ring, and $R_3$ and $R_4$ are unsubstituted or substituted by one or more identical or different radicals selected from the group $C_1$–$C_4$-alkyl, $C_2$–$C_4$-alkenyl, $C_1$–$C_4$-alkoxy, $C_1$–$C_4$-halogenalkyl, $C_1$–$C_4$-hydroxyalkyl, $C_1$–$C_4$-alkoxymethyl or -ethyl, $C_1$–$C_4$-halogenalkoxy, $C_4$–$C_7$-cycloalkyl, $C_4$–$C_7$-cycloalkyloxy, $C_4$–$C_7$-cycloalkylmethyl, $C_4$–$C_7$-cycloalkylmethyloxy, phenyl, phenyloxy, benzyl, benzyloxy, phenylethyl, phenylethyloxy, halogen, —$OR_5$, —$OC(O)R_5$, —$NR_5R_6$, —NH—$C(O)$—$R_5$, —$NR_5$—$C(O)$—$R_6$, —$CO_2R_5$, —$CO_2$—$NH_2$, —$CO_2$—$NHR_5$, —$CO_2$—$NR_5R_6$, wherein $R_5$ and $R_6$, independently of one another, are $C_1$–$C_4$-alkyl, $C_4$–$C_7$-cycloalkyl, $C_4$–$C_7$-cycloalkylmethyl, phenyl or benzyl.

Preferred substituents are methyl, ethyl, n- and isopropyl, n- and tert.-butyl, vinyl, allyl, methyloxy, ethyloxy, n- and isopropyloxy, n-and tert.-butyloxy, trifluoromethyl, β-hydroxyethyl, methoxy- or ethoxymethyl or -ethyl, trifluoromethoxy, cyclohexyl, cyclohexyloxy, cyclohexylmethyl, cyclohexylmethyloxy, phenyl, phenyloxy, benzyl, benzyloxy, phenylethyloxy, phenylethyl, halogen, —OH, —$OR_5$, —$OC(O)R_5$, —$NH_2$, —$NHR_5$, —$NR_5R_6$, —NH—$C(O)$—$R_5$, -$NR_5$—$C(O)$—$R_5$, —$CO_2R_5$, —$CO_2$—$NH_2$, —$CO_2$—$NHR_5$, —$CO_2$—$NR_5R_6$, wherein $R_5$ $R_6$, independently of one another, are $C_1$–$C_4$-alkyl, cyclohexyl, cyclohexylmethyl, phenyl or benzyl.

The aliphatic radical is preferably alkyl which may be linear or branched and contains preferably 1 to 8, more preferably 1 to 4 carbon atoms, or preferably alkenyl or alkenyl which may be linear or branched and preferably contain 2 to 8, more preferably 2 to 4 carbon atoms. If $R_2$ and $R_3$ are alkenyl or alkinyl, the unsaturated bond is preferably in β-position to the O-atom. Examples are methyl, ethyl, n- and isopropyl, n-, iso- and tert.-butyl, pentyl, isopentyl, hexyl, heptyl, octyl, nonyl, decyl, undecyl and dodecyl, vinyl, allyl, ethinyl and propargyl. One preferred group of aliphatic radicals is methyl, ethyl, n- and isopropyl, n-, iso- and tert.-butyl.

The cycloaliphatic radical is preferably cycloalkyl or cycloalkenyl with preferably 3 to 8, more preferable 5 or 6 ring carbon atoms. A few examples are cyclopropyl, cyclobutyl, cyclopentyl, cyclohexyl, cycloheptyl and cyclooctyl, as well as cyclopentenyl, cyclohexenyl and cyclohexadienyl. Cyclopentyl and cyclohexyl are preferred in particular.

The heterocycloaliphatic radical is preferably heterocycloalkyl or heterocycloalkenyl with preferably 3 to 6 carbon atoms, 4 to 7 ring members and hetero atoms selected from the group —O— and —NR'—, wherein R' is $C_1$–$C_8$-alkyl, preferably $C_1$–$C_4$-alkyl, $C_5$ or $C_6$-cycloalkyl, $C_6$–$C_{10}$-aryl, for example phenyl or naphthyl, phenyl or phenylethyl. A few examples are pyrrolidinyl, pyrrolinyl, tetrahydrofuranyl, dihydrofuranyl and piperanzinyl.

The cycloaliphatic-aliphatic radical is preferably cycloalkyl-alkyl or -alkenyl with preferably 3 to 8, more preferably 5 or 6 ring carbon atoms and preferably 1 to 4, or 3 to 4, more preferably 1 or 2, or 3 carbon atoms in the alkyl group or alkenyl group. Examples are cyclopentyl- or cyclohexylmethyl or -ethyl and cyclopentyl- or cyclohexyl-propenyl.

The heterocycloaliphatic-aliphatic radical is preferably heterocycloalkyl-alkyl or -alkenyl with preferably 3 to 6 carbon atoms, 4 to 7 ring members and hetero atoms selected from the group —O— and —NR'—, wherein R' is $C_1$–$C_8$-alkyl, preferably $C_1$–$C_4$-alkyl, $C_5$- or $C_6$-cycloalkyyl, $C_6$–$C_{10}$-aryl, for example phenyl or naphthyl, phenyl or phenylethyl, and preferably 1 to 4, more preferably 1 or 2 carbon atoms in the alkyl group, or 3 to 4, and most preferably 3 carbon atoms in the alkenyl group. Examples are pyrrolidinylmethyl or -ethyl or -propyl, pyrrolinylmethyl or -ethyl or -propyl, tetrahydrofuranylmethyl or -ethyl or -propyl, dihydrofuranylmethyl or -ethyl or -propyl, and piperanzinylmethyl or -ethyl or -propyl.

The aromatic radicals are especially naphthyl, and in particular phenyl.

The aromatic-aliphatic radicals are preferably phenyl- or naphthyl-$C_1$–$C_4$-alkyl or —$C_2$–$C_4$-alkenyl. A few examples are benzyl, naphthylmethyl, β-phenylethyl and β-phenylethenyl.

The heteroaromatic radicals are preferably 5- or 6-membered, optionally condensed ring systems. A few examples are pyridinyl, pyrimidinyl, pyrazinyl, pyrrolyl, furanyl, oxazolyl, imidazolyl, benzofuranyl, indolyl, benzimidazolyl, quinolinyl, isoquinolinyl, quinazolinyl, quinoxalinyl.

The heteroaromatic-aliphatic radicals are preferably 5- or 6-membered, optionally condensed ring systems, which are bonded by one of their carbon atoms to the free bond of an alkyl group or alkenyl group, whereby the alkyl group contains preferably 1 to 4, more preferably 1 or 2 carbon atoms, and the alkenyl group contains preferably 3 to 4, more preferably 3 carbon atoms. A few examples are pyridinylmethyl or -ethyl or -propenyl, pyrimidinylmethyl or -ethyl or -propenyl, pyrrolylmethyl or -ethyl or -propenyl, furanylmethyl or -ethyl or -propenyl, imidazolylmethyl or -ethyl or -propenyl, indolylmethyl or -ethyl or -propenyl.

$R_3$ and $R_4$, together with the N-atom, preferably form a 4- to 8-membered heterocyclic ring, The ring may be ethylenically unsaturated. The ring may be monocyclic rings or polycyclic bridged and/or condensed ring systems, which contain for example 2 to 4 or 2 to 3 rings. A few examples are pyrrolidine, pyrroline, morpholine, indole and piperazine.

Preferred nucleophiles from the group of alcohols and amines are alkanols with 1 to 12 carbon atoms, primary alkylamines with 1 to 12 carbon atoms, and secondary amines with 2 to 16 carbon atoms.

The alcohols and amines may also be used in the form of their alkali metal alcoholates or alkali metal amides, with potassium, sodium and lithium amides and alcoholates being preferred in particular.

Nucleophiles from the group of metallised hydrocarbons and metal cyanides are generally known. The metals may be selected from the group of alkali metals and alkaline earth metals, boron, aluminium, silicon, tin, zinc, manganese and copper. Examples of alkali metals and alkaline earth metals are Li, Na, K, Mg and Ca. Preferred alkali metals and alkaline earth metals are Li, Na, K and Mg.

The metallised cyanides are preferably alkali metal cyanides, copper(I) and zinc dicyanide. Of the alkali metal cyanides, potassium, sodium and lithium cyanides are preferred.

The metallised hydrocarbons are the generally known Grignard compounds, as well as zinc-, copper-, tin-, manganese-, silicon- and boron-organic compounds, which have been described in literature many times. Only hydrocarbon radicals may be bonded to di- to tetravalent metals, or hydrocarbon radicals and halides, hydroxide or also alkoxides. More preferably, the poly-valent metals are hydrocarbon-metal halides, whereby halogen is preferably chlorine, bromine or iodine, as well as hydrocarbon-metal hydroxides or alkoxides with preferably 1 to 6 carbon atoms in the alkoxy group.

The metallised hydrocarbons may correspond, for example, to formula VI,

$$R_7\text{—}Y \quad (VI),$$

wherein $R_7$ signifies a monovalent, saturated or unsaturated aliphatic radical with 1 to 12 carbon atoms, a saturated or unsaturated cycloaliphatic radical with 3 to 8 carbon atoms, a saturated or unsaturated heterocycloaliphatic radical with 3 to 8 ring members and one or two hetero atoms from the group O, S, N and NR', a saturated or unsaturated cycloaliphatic-aliphatic radical with 4 to 12 carbon atoms, a saturated or unsaturated heterocycloaliphatic-aliphatic radical with 3 to 12 carbon atoms and one or two hetero atoms from the group O, S, N and NR', an aromatic radical with 6 to 10 carbon atoms, a hetero-aromatic radical with 4 to 9 carbon atoms and one or two hetero atoms from the group O, S and N, an aromatic-aliphatic radical with 7 to 12 carbon atoms or a hetero-aromatic-aliphatic radical with 5 to 11 carbon atoms and one or two hetero atoms from the group O, S and N, whereby R' is $C_1$–$C_8$-alkyl, preferably $C_1$–$C_4$-alkyl, $C_5$- or $C_6$-cycloalkyl, $C_6$–$C_{10}$-aryl such as phenyl or naphthyl, or phenyl or phenylethyl.

$R_7$ are unsubstituted or substituted by one or more, identical or different radicals selected from the group $C_1$–$C_4$-alkyl, $C_1$–$C_4$-Alkoxy, $C_1$–$C_4$-alkoxy-$C_1$–$C_4$-alkyl, $C_4$–$C_7$-cycloalkyl, $C_4$–$C_7$-cycloalkyloxy, $C_4$–$C_7$-cycloalkylmethyl, $C_4$–$C_7$-cycloalkylmethyloxy, phenyl, phenyloxy, benzyl, benzyloxy, phenylethyl, phenylethyloxy, halogen, —$OR_5$, —$OC(O)R_5$, —$NR_5R_6$, —NH—C(O)—$R_5$, —$NR_5$—C(O)—$R_6$, —$CO_2R_5$, —$CO_2$—$NH_2$, —$CO_2$—$NHR_5$, —$CO_2$—$NR_5R_6$, wherein $R_5$ and $R_6$, independently of one another, are $C_1$–$C_4$-alkyl, $C_4$–$C_7$-cycloalkyl, $C_4$–$C_7$-cycloalkyl methyl, phenyl or benzyl, Y is Li, Na, K, MgZ, ZnZ, CuZ, SnZ, $BZ_2$, $AlZ_2$, $SiZ_3$, or $R_7SiZ_2$, and Z signifies fluoride, chloride, bromide, iodide, —OH or $C_1$–$C_4$-alkoxide.

The heterocyclic radicals are bonded to the metal by a ring carbon atom. Y preferably signifies Li, Na, K, MgZ, ZnZ and MnZ, wherein Z is preferably chloride or bromide, or $BZ_2$, wherein Z is preferably fluoride, —OH or $C_1$–$C_6$-alkoxide. The preferences and examples indicated above for $R_3$ and its substituents also apply to $R_7$. Alkenyl radicals and alkinyl radicals are bonded directly to Y.

Within the context of the invention, the CH-acidic compounds are understood to be those organic compounds in which at least one electron-attracting and mesomerising group is bonded to at least one carbon atom. Such groups are, for example, keto, thioketo, aldehyde, carboxylate, carbamide, nitrile, sulfine, sulfone, nitro, phosphonate and phosphonium groups. Preferred groups are keto, carboxylate, carbamide and nitrile groups. The CH-acidic compounds may contain for example 1 to 4, preferably 1 or 2 groups. Especially preferred CH-acidic compounds are malonic acid diesters, malonic acid diamides, malonic acid dinitrile and keto compounds, most preferably diketones and β-ketocarboxylates with 1 to 8 carbon atoms in the ester group.

The CH-acidic compounds may be, for example, saturated or unsaturated aliphatic, cycloaliphatic, heteroaliphatic and heterocycloaliphatic compounds with hetero atoms selected from the group O, S and N, which contain 2 to 30, preferably 2 to 20, most preferably 2 to 16 carbon atoms. The cycloaliphatic compounds may be mono- or polycyclic condensed and/or bridged rings, which contain 3 to 16, preferably 3 to 12, most preferably 4 to 8 ring members. Aromatics and/or heteroaromatics may be condensed onto one or more rings. The compounds may be unsubstituted or substituted by $C_1$-$C_4$-halogenalkyl, —$N(C_1$–$C_4$-alkyl)$_2$, —$SO_3M$, —COOM, —COOH, $C_5$–$C_{12}$-cycloalkyl, $C_5$–$C_{12}$-heterocycloalkyl with 1 to 3 hetero atoms selected from the group O, S and N, $C_1$–$C_6$-alkoxy, $C_6$–$C_{12}$-aryl, $C_4$–$C_{11}$-heteroary with 1 to 3 hetero atoms selected from the group O, S and N, $C_7$–$C_{12}$-aralkyl, $C_5$–$C_{12}$-heteroaralkyl with 1 to 3 hetero atoms selected from the group O, S and N, whereby M signifies Li, Na or K. Suitable substituents for the cyclic radicals are also $C_1$–$C_4$-alkyl. Cyclic substituents may be unsubstituted or substituted by halogen (preferably F), $C_1$–$C_4$-alkyl, $C_1$–$C_4$-halogenalkyl or $C_1$–$C_4$-alkoxy. Examples of saturated or unsaturated, aliphatic, cycloaliphatic, heteroaliphatic and heterocycloaliphatic radicals have already been mentioned.

The CH-acidic compounds within the context of the invention are also understood to be acetylene and monosubstituted acetylene. The substituents may be those defined for $R_7$, including the preferences.

The nucleophiles used according to the invention are known compounds or compounds which may be prepared by known or analogous methods. Metallisation is achieved in known manner, by exchanging hydrogen in acidic compounds (OH, NH or acidic CH functions) for strong bases (for example alkali metal alcoholates), or by exchanging halogen for metals, or by exchanging metals. Metallisation of acidic compounds may take place separately prior to carrying out the process according to the invention, or prior to the reaction in situ. The preparation of Grignard compounds and other organometallic compounds is generally known. The preparation of metallised hydrocarbons by reacting alkylcarbonyl compounds or other CH-acidic compounds with strong bases (for example alkali metal alcoholates and alkali metal amides) is also generally known.

Variant b)

Carbon monoxide is introduced into the reaction container in general under high pressure and the reaction is carried out under high pressure. Within the context of the invention, high pressure may mean 0.01 to 10 MPa (megapascals), preferably 0.5 to 5 MPa.

Water, alcohols, ammonia and amines are generally used in eqivalent amounts, based on the leaving groups present in the aromatics. An excess may also be used, and these reactants can even simultaneously serve as solvents. It is preferable to use 1 to 10, especially 1 to 5 equivalents per leaving group.

The alcohols and amines in question may be the alcohols and amines described in variant a), including the preferences.

The alcohols and amines may correspond to formula Va,

$$R_3\text{—}X_aH \qquad (Va),$$

wherein $X_a$ is —O— or —N—$R_4$, and $R_3$ and $R_4$ have the significances given for the compounds of formula V, including the configurations and preferences.

Especially preferred in variant b) are water, ammonia, alkanols with 1 to 12 carbon atoms, primary alkylamines with 1 to 12 carbon atoms, and secondary amines with 2 to 16 carbon atoms.

Variant c)

Suitable vinyl compounds are known in large number. They may be for example alkenes, cycloalkenes or mono-substituted or disubstituted ethylene. Vinyl compounds of formula VII are preferred,

$$R_8HC\text{=}CHR_9R_{10} \qquad (VII),$$

wherein $R_9$ is H, $C_1$–$C_6$-alkyl, $C_1$–$C_6$-alkoxy, $C_1$–$C_6$-hydroxyalkyl, $C_1$–$C_6$-aminoalkyl, $C_1$–$C_6$-halogenalkyl, $C_1$–$C_6$-cyanoalkyl, —$C_1$–$C_6$-alkyl-X with X equal to —COOH, —COOM, —COO—$C_1$–$C_4$-alkyl, —CO—$NH_2$, —CO—NH—$C_1$–$C_4$-alkyl, —CO—N($C_1$–$C_4$-alkyl)$_2$; $C_3$–$C_8$-cycloalkyl, $C_3$–$C_8$-cycloalkoxy, $C_3$–$C_8$-hydroxycycloalkyl, $C_3$–$C_8$-aminocycloalkyl, $C_3$–$C_8$-cyanocycloalkyl, $C_3$–$C_8$-halogencycloalkyl, —$C_3$–$C_8$-cycloalkyl-X with X equal to —COOH, —COOM, —CN, —COO—$C_1$–$C_{14}$-alkyl, —CO—$NH_2$, —CO—NH—$C_1$–$C_4$-alkyl, —CO—N($C_1$–$C_4$-alkyl)$_2$; $C_1$–$C_6$-alkyl-CO—, $C_3$–$C_8$-cycloalkyl-CO; $C_6$–$C_{16}$-aryl, $C_6$–$C_{16}$-aryloxy, $C_6$–$C_{16}$-hydroxyaryl, $C_6$–$C_{16}$-aminoaryl, $C_6$–$C_{16}$-cyanoaryl, —$C_6$–$C_{16}$-aryl-X with X equal to —COOH, —CN, —COOM, —COO—$C_1$-$C_{14}$-alkyl, —CO—$NH_2$, —CO—NH—$C_1$–$C_4$-alkyl, —CO—N($C_1$–$C_4$-alkyl)$_2$; $C_4$–$C_{16}$-heteroaryl, $C_4$–$C_{16}$-heteroaryloxy, $C_6$–$C_{16}$-hydroxyheteroaryl, $C_6$–$C_{16}$-aminoheteroaryl, $C_6$–$C_{16}$-cyanoheteroaryl, —$C_6$–$C_{16}$-heteroaryl-X with X equal to —COOH, —COOM, —COO—$C_1$–$C_{14}$-alkyl, —CO—$NH_2$, —CO—NH—$C_1$–$C_4$-alkyl, —CO—N($C_1$–$C_4$alkyl)$_2$; or —CN, —COOH, —COOM, —COO—$C_1$–$C_{14}$-alkyl, —COH, —CO—$C_1$–$C_{14}$-alkyl, —CO—$NH_2$, —CO—NH—$C_1$–$C_4$-alkyl, —CO—N($C_1$–$C_4$-alkyl)$_2$, $C_1$–$C_4$-alkyl-COO—, —O—$C_1$–$C_4$-alkyl, —NH—$C_1$–$C_4$-alkyl, —N($C_1$–$C_4$-alkyl)$_2$, $R_8$, independently, has the same significance as $R_4$, $R_{10}$, independently, has the same significance as $R_4$, or $R_8$ and $R_9$ together are linear or branched, unsubstituted or substituted alkylene, and $R_{10}$ has the above significances, and M is Li, Na or K.

Alkylene may contain for example 1 to 10 carbon atoms. A few examples are methylene, ethylene, 1,2-und 1,3-propylene, 1,2-, 1,3- and 1,4-butylene, pentylene, hexylene, heptylene, octylene, nonylene and decylene.

Substituents for $R_8$ and $R_9$ together as alkylene may be selected, for example, from the significances for $R_8$.

Preferred compounds of formula VII are ethylene, propylene, butene, pentene, hexene, acrylates or methacrylates with 1 to 4 carbon atoms in the ester group, acrylonitrile, crotonic acid esters with 1 to 4 carbon atoms in the ester group, vinyl ketones such as vinyl methyl ketone, vinyl ethyl ketone, vinyl-n- or -isopropyl ketone, vinyl-n- or -isobutyl ketone, allyl alcohol, acrylic acid, methacrylic acid, cyclohexene, cyclopentene, cycloheptene, cyclooctene, styrene and styrenes substituted by OH, F, Cl, CN, —COOH, —$SO_3H$, $C_1$–$C_6$-alkyl, $C_1$–$C_6$-alkoxy; α-methylstyrene and α-methylstyrenes substituted by OH, F, Cl, CN, —COOH, —$SO_3H$, $C_1$–$C_6$-alkyl, $C_1$–$C_6$-alkoxy; heteroaromatic vinyl compounds such as vinyl pyridine, vinyl pyrrolidone and vinyl pyrrole, and corresponding heteroaromatic vinyl compounds substituted by OH, F, Cl, CN, —COOH, —$SO_3H$, $C_1$–$C_6$-alkyl, $C_1$–$C_6$-alkoxy.

In variant c), the hydrocarbon- and hetero-aromatics described for variants a) and b) may be used, including the preferences and configurations.

The vinyl aromatics produced by the process according to the invention may be described by the formula $ArR_8C\text{=}CR_9R_{10}$, wherein Ar is unsubstituted or substituted aryl or heteroaryl, and $R_8$, $R_9$ and $R_{10}$ have the significances given above.

Process Conditions for Variants a), b) and c)

The process according to the invention is carried out in the case of variants b) and c) and may be carried out in the case of variant a) in the presence of an inorganic base or organic nitrogen base. Suitable inorganic bases are, for example alkali metal hydroxides, alcoholates, carbonates, hydrogen carbonates, oxides, phosphates, carboxylates, silicates; and alkaline earth metal hydroxides, alcoholates, carbonates, hydrogen carbonates, oxides, phosphates, carboxylates and silicates. Specific examples are LiOH, NaOH, KOH, Mg(OH)$_2$, Ca(OH)$_2$, Ba(OH)$_2$, CaO, MgO, lithium, potassium and sodium tertiary butylate, lithium, potassium, sodium and cesium carbonate, lithium, sodium and potassium amides, lithium, sodium and potassium hydride. Suitable organic nitrogen bases are secondary and tertiary amines, for example diethyl-, trimethyl-, triethyl-, methyldiethyl-, tri-n-propyl, tri-n-butylamin, diethyl-isopropylamine, as well as cyclic tertiary amines, for example 2H-pyrrole, imidazole, pyrazole, pyridine, pyrazine, pyrimidine, pyridazine, 3H-indole, 1H-indazole, purine isoquinoline, quinoline, phthalazine, naphthydrine, quinoxaline, quinazoline, pteridine, acridine, phenanthroline, phenazine, imidazoline, triazine, 2-piccoline, lutidine, benzimidazole, methylimidazole, pyrazole, 4-dimethylaminopyridine, 4-pyrrolidinopyridine, 1,3,5-triazine and 4-methylaminopyridine.

Preference is given to Li, Na, K, Cs carbonate, hydrogen carbonate, acetate, Na and K phosphate, Na t-butylate, CaO, MgO, triethylamine and tributylamine. Particular preference is given to sodium or potassium carbonate, sodium or potassium-$C_1$–$C_4$-carboxylate, trimethylamine, triethylamine or tributylamine.

When using alcohols, thiols, amines and CH-acidic compounds as nucleophiles in variant a), it is expedient and advantageous to concurrently use a base, preferably carbonates, alkoxides, phosphates and amides.

Of the metallised hydrocarbons in variant a), the addition of bases is indicated particularly in the case of boron and silicon compounds, preferably fluorides, carbonates, phosphates, hydroxides and alkoxides. It may be appropriate, if necessary, to use a metal halide salt, such as zinc, magnesium, manganese, copper halides as co-catalysts. The amount of co-catalyst will then be 0.1 to 150%, based on the metallised hydrocarbon, preferably 1 to 10%.

When using acetylenes as CH-acidic compounds, it may be advantageous to add copper salts as co-catalysts, and bases, for example tertiary amines.

The process according to the invention may be carried out without or in the presence of an inert solvent. Suitable solvents are, for example aliphatic, cycloaliphatic and aromatic hydrocarbons (pentane, hexane, petroleum ether, cyclohexane, methylcyclohexane, benzene, toluene, xylene), aliphatic halogen-hydrocarbons (methylene chloride, chloroform, di- and tetrachloroethane), nitriles (acetonitrile, propionitrile, benzonitrile), ethers (diethylether, dibutylether, tert.-butylmethylether, ethylene glycol dimethylether, ethylene glycol diethylether, diethylene glycol dimethylether, tetrahydrofuran, dioxane, ketones (acetone, methyl isobutyl ketone), carboxylates and lactones (ethyl and methyl acetate, valerolactone), N-substituted lactams (N-methylpyrrolidone), carboxamides (dimethylamide, dimethylformamide), acyclic ureas (tetramethylurea) or cyclic ureas (dimethyl imidazolidinone), and sulfoxides and sulfones (dimethyl sulfoxide, dimethyl sulfone, tetramethylene sulfoxide, tetramethylene sulfone) and alcohols (methanol, ethanol, propanol, butanol, ethylene glycol monoethyl ether, diethylene glycol monomethyl ether) and water. The solvents may be used on their own or in a mixture of at least two solvents.

Preferred solvents are N,N-alkylated carboxamides and lactams, such as dimethyl-acetamide, dimethylformamide, N-methylpyrrolidone, as well as propylene carbonate, dimethylsulfoxide, dioxane, acetonitrile, toluene, xylene, dimethylimidazolidinone (DMI) and 1,2-dimethyl-3,4,5,6-tetrahydro-pyrimidinone (DMPU).

The reaction may be carried out at normal pressure or at slight excess pressure. Elevated temperature in the context of the invention can mean a temperature range of 30 to 250° C., preferably 50 to 200° C., most preferably 80 to 160° C.

Pd complexes of phosphines and their preparation are known, and the complexes used according to the invention can be described by the formula Pd(secondary phosphine)$_2$ or Pd(secondary phosphine)$_4$. The catalytically active variants in the reaction according to the invention may deviate from these formulae.

Pd catalysts are generally obtained from Pd(II) or Pd(0) compounds by complexing with secondary monophosphines. Suitable Pd compounds are, for example, palladium dihalides and diacetate, palladium sulfate, Pd(acetyl acetonate)$_2$, Pd$_2$(dibenzylidene acetone)$_3$, Pd(CH$_3$CN)$_2$X$_2$, Pd(PhCN)$_2$X$_2$, Pd(allyl)Cl, PdO, Pd(OH)$_2$, Pd(NO$_3$)$_2$, Na$_2$PdCl$_4$, H$_2$PdCl$_4$ and palladacyclic compounds of formula IX.

The catalyst may be prepared in various ways. For example, the catalyst may be produced separately, and then used as an isolated Pd complex. In the case, it may be expedient to additionally add secondary monophosphines to the reaction mixture, for example up to a ten times excess, based on the Pd-secondary monophosphine complex. The isolated catalyst may be presented, optionally in a solvent, and then the reactants and a base added, or the isolated catalyst may be added to the optionally dissolved reactants and a base, in order to start the reaction and bring it to an end by means of heating.

It is especially advantageous in the process according to the invention for the catalyst to be produced in situ, whereby a Pd(II) salt, a Pd(II) complex salt or a Pd(0) complex optionally in a solvent is presented or prepared, and then at least equimolar amounts of the secondary monophosphine or an excess (for example an equimolar excess) are added. Then, an aromatic, a nucleophile and a base, and optionally further solvent, are added to this mixture, the reaction is started by heating and is brought to an end at an elevated temperature. The procedure involved in this in situ production of the catalyst may also be as follows: an optionally heated solution of all reactants and a base is presented, and then a Pd(0) or Pd(II) compound and then the secondary monophosphine, or first the secondary monophosphine and then a Pd(0) or Pd(II) compound are added after one another. Then, the desired reaction temperature is selected and the reaction brought to an end. In a further variant for the in situ formation of the catalyst, a Pd(0) or Pd(II) compound and a secondary monophosphine with or without solvent are placed in an aromatic containing a leaving group, the mixture is conditioned with heating and then the reactants and reaction assistants are added.

As described above, the palladium catalyst can also be formed from a heterogeneous catalyst precursor, for example colloidal Pd(0), Pd(0) applied to carrier materials or Pd(II) compounds applied to carrier materials, such as PdO or Pd(II) salts. Suitable carrier materials are for example inorganic metal oxides, silicates and carbon.

The catalyst may be used in a concentration of 0.0001 mol % to 10 mol %, preferably in a concentration of 0.001 mol % to 5 mol %, most preferably 0.01 mol % to 3 mol %, based on the aromatic compound. The molar ratio of phosphine to palladium in the reaction mixture may be 1:1 to 100:1, preferably 1:1 to 10:1, more preferably 1:1 to 4:1.

The inorganic bases and organic nitrogen bases can be used in catalytic to stoichiometric amounts or in an excess, based on the aromatics. The amount may be for example 0.5 to 50, preferably. 0.9 to 5, most preferably 1 to 3 equivalents, based on the aromatic compound. Owing to the sensitivity to air of secondary monophosphines, the process is preferably carried out in an oxygen-free inert gas atmosphere. Suitable inert gases are for example nitrogen and noble gases, such as helium, neon and argon.

Another object of the invention is the use of Pd-phosphine complexes with secondary aliphatic monophosphines as catalysts for the coupling of a) nucleophiles selected from the group alcohols, thiols, amines, metallised hydrocarbons, CH-acidic compounds and metal cyanides, or of b) carbon monoxide mixed with water, alcohols, ammonia, primary or secondary amines, to organic compounds selected from the group of leaving-group-containing aromatics, hetero-aromatics with a C-bonded leaving group, aromatic or hetero-aromatic methyl compounds with a leaving group bonded to the methyl group, ethylenically unsaturated organic compounds with a C-bonded leaving group, or organic allyl compounds with a leaving group in allyl position, or c) vinyl compounds with leaving-group-containing aromatics, whilst cleaving the leaving group.

Another object of the invention is a kit of (a) an optionally dissolved Pd(II) salt, a Pd(II) complex salt or a Pd(0) complex, and (b) an optionally dissolved secondary monophosphine, which are found in separate containers. The molar ratio of phosphine to palladium may be 1:1 to 100:1, preferably 1:1 to 10:1, more preferably 1:1 to 4:1. The components may also contain an inert solvent, whereby the concentration of Pd(II) salt, Pd(II) complex salt or Pd(0) complex, or secondary monophosphine, may be 1 to 90% by weight, based on the composition containing a solvent. Suitable solvents have already been named. The kit is especially suitable for the preparation and in situ production of catalyst precursors and catalysts.

It has also been found that certain palladacyclic complexes with secondary phosphine groups as a ligand are easy to produce and isolate, and even have surprisingly high stability when in contact with air. These are predominantly crystalline compounds. They are eminently suitable as catalysts in the process according to the invention and can be handled in the air without problems and without taking precautionary measures.

A further object of the invention is therefore compounds of formula VIII,

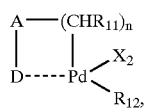
(VIII)

wherein

A signifies a bivalent aromatic hydrocarbon radical;

D represents a substituent which contains atoms coordinating with palladium, and D is bonded to radical A in ortho position to the group —$CHR_{11}$—;

$X_2$ is the anion of a monobasic inorganic acid or organic acid;

n is 0 or 1;

$R_{11}$ signifies hydrogen or $C_1$–$C_4$-alkyl;

$R_{12}$ represents a secondary monophosphine with aliphatic, branched or cyclic substituents; and A and D, together with the group —$CHR_{11}$— and the palladium atom, form a 4- to 6-membered ring.

A as an aromatic hydrocarbon radical preferably contains 5 to 18, most preferably 6 to 12 carbon atoms. A may be for example phenylene, naphthylene or cyclopentadienylene in a ferrocene frame. A most preferably signifies 1,2-phenylene.

The monobasic anion $A_2$ may be for example Cl, Br or I, $ClO_4$, $PF_6$, $SbCl_6$, anions of $C_1$–$C_8$-carboxylic acids (formate, acetate, propionate and benzoate), anions of C–$C_8$-halogen-carboxylic acids (chloroacetate, fluoroacetate, trichloroacetate, trifluoroacetate), anions of $C_1$–$C_8$-sulfonic acids (methyl sulfonate, phenyl sulfonate, tosylate), anions of $C_1$–$C_8$-halogen-sulfonic acids (trifluorosulfonate). $X_2$ is preferably Br and most preferably Cl.

If $R_{11}$ signifies alkyl, it may be methyl, ethyl, n- or isopropyl or n-butyl. $R_{11}$ most preferably signifies hydrogen.

$R_{12}$ is preferably secondary monophosphines of formula I, including the preferences and configurations.

A and D, together with the group —$CHR_{11}$— and the palladium atom, form a 5- to 6-membered ring.

The coordinating atoms in the substituent D may be for example O, S, N and P, with O and N being preferred.

The coordinating atoms may be bonded directly to the radical A, for example as —OH, SH, or unsubstituted or mono- or disubstituted amino or phosphine. Suitable substituents are also hydroxy-, thio-, mono- or disubstituted amino- or phosphineomethyl or -eth-2-yl. Suitable substituents for amino and phosphino are for example $C_1$–$C_8$- and especially $C_1$–$C_4$-alkyl (such as methyl, ethyl, propyl or butyl), $C_4$–$C_8$- and especially $C_5$–$C_6$-cycloalkyl, $C_5$–$C_{12}$- and especially $C_6$–$C_{12}$-cycloalkylalkyl, $C_6$–$C_{14}$- and especially $C_6$–$C_{10}$-aryl, and $C_7$–$C_{18}$- and especially $C_6$–$C_{12}$-aralkyl. The chelating atoms preferably contain no hydrogen atoms. The groups —OH and —SH are therefore preferably substituted by aliphatic radicals, for example $C_1$–$C_8$- and especially $C_1$–$C_4$-alkyl (such as methyl, ethyl, propyl or butyl), $C_4$–$C_8$- and especially $C_5$–$C_6$-cycloalkyl, or $C_5$–$C_{12}$- and especially $C_6$–$C_{12}$-cycloalkylalkyl.

Further suitable substituents D are also azo and imino groups of formulae —N═N—$R_{13}$ and —$CH_2$—N═N—$R_{13}$ as well as —($R_{14}$)CH═N—$R_{13}$, —N═CH—$R_{13}$ and —$CH_2$—N═CH—$R_{14}$, wherein $R_{13}$ signifies $C_1$–$C_4$-alkyl, phenyl, cyclohexyl or benzyl, and $R_{14}$ is H, $C_1$–$C_8$-alkyl, $C_5$–$C_6$-cycloalkyl, $C_6$–$C_{10}$-aryl or $C_6$–$C_{12}$-aralkyl. Other substituents D are for example those of formula —NH—C($R_{14}$)═$NR_{13}$, wherein $R_{13}$ and $R_{14}$ are defined as above, and those of formula —$X_4$-$CH_2$—$X_5$—$R_{15}$, wherein $X_4$ signifies —O—, —S— or —$NR_{16}$—, $R_{15}$ is H or $C_1$–$C_4C_1$–$C_4$-alkyl. The substituent may also correspond to formula ($R_{14}$)C(O)—$NR_{13}$—, wherein $R_{13}$ and $R_{14}$ are defined as above. The substituent may also correspond to formula —CH═N—$OR_{13}$ or —CH═N—N($R_{13}$)$_2$, wherein $R_{13}$ is defined as above.

The substituent D may also be aliphatic heterocycles, which contain a group —$NR_{13}$— or —$PR_{13}$— in the ring in a α-position to the bond, whereby $R_{13}$ is defined as above. The heterocycle may contain 3 to 8, preferably 4 to 6 ring atoms. A few examples are pyrrolidin-2-yl, piperazin-2-yl, oxazolidin-2-yl and morpholin-2-yl.

The substituent D may also be those of formulae

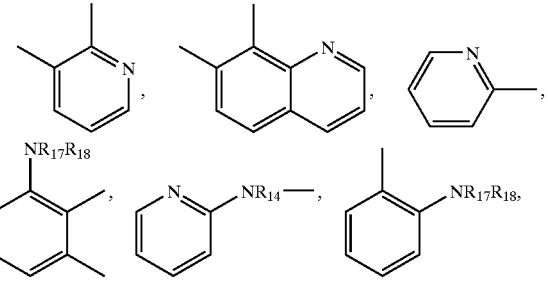

wherein $R_{14}$ is defined as above, and $R_{17}$ and $R_{18}$ independently have the significance of $R_{13}$. Two free bonds in the formulae means that the substituent in 1,2-position is condensed to the aromatic substance A.

The compounds of formulae VIII may be obtained in known manner, by reacting compounds of formula IX,

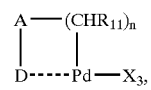
(IX)

or its binuclear derivatives with a secondary phosphine $R_{12}$, wherein A, D, $R_{11}$ and $R_{12}$ have the significances given for formula VIII, and $X_3$ is the anion of a monobasic inorganic or organic acid.

The reaction is suitably carried out at temperatures of for example 0 to 250° C. and under a protective gas atmosphere (noble gases, nitrogen). The presence of solvents is an advantage. Suitable solvents have already been named. Preferred solvents are halogenated hydrocarbons and ether. The secondary diphosphine is added in equimolar amounts or in a slight excess. Isolation and purification are undertaken in known manner. If $X_3$ is the anion of an organic acid, halogen donors are added, preferably in excess. Suitable halogen donors are metal or onium halides, for example alkali metal halides, such as LiCl, LiBr, NaCl or NaBr.

The compounds of formula IX are known or may be produced in analogous manner. The compounds are described for example by M. Pfeffer in Recl. Trav. Chim. Pays-Bas 109, pages 567 to 576 (1990), or by J. Tsuji in Palladium Reagents and Catalysts, pages 87–96 (1996), John Wiley & Sons (New York).

The nucleophile-substituted organic compounds produced according to the invention are valuable intermediates in the preparation of pharmaceutical and pesticidal active ingredients, see for example U.S. Pat. No. 5,919,930, EP-A-0385210, U.S. Pat. No. 5,536,870 (preparation of Naproxen) and EP-A-0376516 (Nabumeton), as well as optical brighteners (EP-A-0873989, intermediate for optical brighteners) and UV absorbers (U.S. Pat. No. 5,187,303).

The following examples illustrate the invention more fully.

a) Preparation of Catalysts

Example A1

Dinorbornylphosphine-{2-(N,N-dimethyl-2'-amino-biphenyl)-C,N}palladium-(II)chloride Di-$\mu$-chloro-bis{2-(N,N-dimethyl-2'-amino-biphenyl)-C,N}dipalladium(II) (338 mg, 0.5 mmols) is placed in 20 ml of methylene chloride and gassed with argon. Dinorbornylphosphine (222 mg, 1 mmols, 50%-ig in toluene) is added and stirred for 10 minutes. The reaction mixture is filtered through Celite and the solvent distilled off in a vacuum. The residue is stirred with hexane. 0.56 g (100%) of the title compound are obtained as colourless crystals.

Example A2

Diadamantylphosphine-{2-(N,N-dimethyl-2'-amino-biphenyl)-C,N}palladium-(II)chloride Di-$\mu$-chloro-bis{2-(N,N-dimethyl-2'-amino-biphenyl)-C,N}dipalladium(II) (23 mg, 0.03 mmols) and diadamantylphosphine (20 mg, 0.07 mmols) are dissolved in 0.5 ml of chloroform. Hexane is slowly condensed in and 40 mg (95%) of the title compound are obtained as yellow crystals.

Example A3

Dicyclohexylphosphine-{2-(6-phenyl-pyridyl)-C,N}palladium(II)chloride

Di-$\mu$-acetato-bis{2-(2-phenyl-pyridyl)-C,N}dipalladium (II) (64 mg, 0.1 mmols) and lithium chloride (42 mg, 1 mmol) are suspended in 5 ml of diethylether under argon. After one hour, dicyclohexylphosphine (50 mg, 0.25 mmols) is added and stirring effected for two hours at room temperature. The reaction mixture is filtered and the solvent distilled off in a vacuum. The residue is recrystallised from methylene chloride/diethyl ether/hexane. The title compound is obtained as yellow crystals in a yield of 50 mg (51%).

Example A4

Di-t-butylphosphine-{1-(N,N-dimethyl-8-amino-naphtyl)-C,N}palladium(II)-chloride Di-$\mu$-acetato-bis{1-(N,N-dimethyl-8-amino-naphtyl)-C,N}dipalladium(II) (67 mg, 0.1 mmols) and lithium chloride (42 mg, 1 mmol) are suspended in 5 ml of diethylether under argon. After one hour, di-t-butyl phosphine (30 mg, 0.2 mmols) is added and stirring effected for two hours at room temperature. The reaction mixture is filtered and the solvent distilled off in a vacuum. The residue is recrystallised from methylene chloride/hexane. The title compound is obtained as brown crystals in a yield of 28 mg (30%).

Example A5

Di-t-butylphosphine-{o-(di-o-tolylphosphino)benzyl-C,P}palladium(II)chloride

Di-$\mu$-acetato-bis{o-(di-o-tolylphosphino)benzyl-C,P}dipalladium(II) (94 mg, 0.1 mmols) and lithium chloride (42 mg, 1 mmol) are suspended in 5 ml of diethylether under argon. After one hour, di-t-butyl phosphine (30 mg, 0.2 mmols) is added and stirring effected for two hours at room temperature. The reaction mixture is filtered and the solvent distilled off in a vacuum. The title compound is obtained as a yellow oil in a yield of 115 mg.

Example A5

Di-t-butylphosphine-{o-acetylamino-phenyl-C,O}palladium(II)chloride

Di-($\mu$-acetato)-bis{o-acetylamino-phenyl-C,O}dipalladium(II) (60 mg, 0.1 mmols) and lithium chloride (42 mg, 1 mmol) are suspended in 5 ml of diethylether under argon. After one hour, di-t-butyl phosphine (30 mg, 0.2 mmols) is added and stirring effected for two hours at room temperature. The residue is recrystallised from diethyl ether/hexane. The title compound is obtained as colourless crystals in a yield of 59 mg (70%).

B) Examples on Variant a)

Example B1

Preparation of p-tolyl-malonic Nitrile 181 mg, 2.75 mmols of malic dinitrile are placed in 13 ml of xylene under argon. Sodium tert.-butanolate (720 mg, 7.5 mmols) is added and stirred for one hour. 4-bromotoluene (427 mg, 2.5 mmols) and a mixture of a 0.01 M PdCl$_2$ solution in DMA (dimethyl acetamide) (0.25 mml) and dinorbornyl phosphine (3.9 mg, 0.017 mmols) in 1 ml of xylene are dispensed in after one another. The reaction mixture is stirred for 16 hours at 160° C. and then cooled. The yield determined in the reaction mixture by liquid chromatography is 100% (LC).

Example B2

Preparation of p-tolyl-malonic Nitrile

Malic dinitrile (1,45 g, 22 mmols) is placed in 140 ml of DMA under argon, and sodium tert.-butanolate (5.94 g, 60 mmols) is added and stirred for one hour. 4-chlorotoluene (2.53 g, 20 mmols) and a mixture of 8 ml of a 0.025 M PdCl$_2$ solution in DMA (0.2 mmols) and diadamantyl phosphine (180 mg, 0.6 mmols) are dispensed in after one another. The reaction mixture is stirred for 16 hours at 140° C. and then cooled. The reaction solution is rendered basic with 200 ml of 1 M NaOH and extracted with diethyl ether. The water phase is adjusted to pH 1-2 with 1M HCl. The precipitated product is filtered off and washed with water. The yield is 1.1 g (39%).

Example B3

Preparation of 4-methoxy-phenyl Malic Nitrile

Malic dinitrile (1.45 g, 22 mmols) is placed in 140 ml of DMA under argon, and sodium tert.-butanolate (5.94 g, 60 mmols) is added and stirred for one hour. 4-chloroanisole (2.85 g, 20 mmols) and a mixture of 8 ml of a 0.025 M PdCl$_2$ solution in DMA (0.2 mmols) and diadamantyl phosphine (180 mg, 0.6 mmols) are dispensed in after one another. The reaction mixture is stirred for 16 hours at 140° C. and then cooled. The reaction solution is rendered basic with 200 ml of 1M NaOH and extracted with diethyl ether. Afterwards, the water phase is adjusted to pH 1–2 with 1M HCl. The precipitated product is filtered off and washed with water. The yield is 2.3 g (74%).

Example B4

Preparation of 2-pyridyl malic nitrile

Malic dinitrile (1.45 g, 22 mmols) is placed in 140 ml of DMA under argon, and sodium tert.-butanolate (5.94 g, 60 mmols) is added and stirred for one hour. 2-chloropyridine (2.27 g, 20 mmols) and a mixture of 8 ml of a 0.025 M $PdCl_2$ solution in DMA (0.2 mmols) and diadamantyl phosphine (180 mg, 0.6 mmols) are dispensed in after one another. The reaction mixture is stirred for 16 hours at 140° C. and then cooled. The reaction solution is adjusted to pH 1–2 with 1 M HCl. The water phase is extracted with diethyl ether. The ether phases are concentrated and the product purified by column chromatography. The yield is 0.7 g (15%).

Example B5

Preparation of 4-methoxybiphenyl

Phenylboric acid (366 mg, 3.0 mmols), palladium acetate (4.49 mg, 0.02 mmols), diadamantyl phosphine (12.1 mg, 0.04 mmols) and potassium triphosphate (1.273 g, 6 mmols) are placed in 6 ml of dioxane and water (0.18 ml, 10 mmols) under argon. The reaction mixture is heated in an oil bath of 100° C. and stirred for 5 minutes. Afterwards, 4-chloroanisole (0.27 ml, 2 mmols) is added. The reaction mixture is then stirred for 18 hours at 100° C. and subsequently cooled. The title compound is purified by flash chromatography over silica gel. The yield is 84%.

Example 6

Synthesis of Various Diaryl Compounds

Phenylboric acid (0.46 g, 3.75 mmols), 2-chloropyridine (0.28 g, 2.5 mmols) and potassium phosphate (1.9 g, 7.5 mmols) are placed under argon, and dioxane (6.5 ml) and water (12.5 mmols) are added. The mixture is heated with an oil bath (100° C.) and a solution of di-µ-chloro-bis-{2-(N,N-dimethyl-2'-amino-biphenyl)-C,N}palladium(II) (9 mg, 0.013 mmol) and dinorbornylphosphine (8.3 mg, 0.038 mmol) in 1 ml of dioxane is added. After a reaction time of 16 hours, the reaction mixture is mixed with water and extracted with tert.-butylmethyl ether. The organic phase is dried and the solvent distilled off in a vacuum. The residue is purified by bulb tube distillation. The yield of 2-phenylpyridine is 0.23 g (59%).

Examples B7 to B10

The examples are carried out analogously to example B6 (purification by chromatography). The results are given in table 1.

TABLE 1

| Ex. | aryl chloride | aryl boric acid | product | yield (%) |
|---|---|---|---|---|
| B7 | 1-chloro-naphthalene | phenyl boric acid | 1-phenylnaphthalene | 47 |
| B8 | 4-chloronitro-benzene | o-tolyl boric acid | 4-nitro-2'-methyl-biphenyl | 69 |
| B9 | 3-chlorobenzoic acid ethyl ester | phenyl boric acid | 3-biphenyl-carbo-oxylic-acid methyl ester | 89 |
| B10 | 2-chlorothiophene | phenyl boric acid | 2-phenylthiophene | 25 |

Example B11

Reaction with Isolated dinorbornylphosphine{2-(N,N-dimethyl-2'-amino-biphenyl)-C,N}palladium(II)chloride as Catalyst Potassium phosphate (0.76 g, 3 mmols) is placed under argon, and a solution of phenyl boric acid (0.18 g, 1.5 mmols), 4.chloroanisole (0.14 g, 1 mmol) and water (90 mg, 12.5 mmols) in 2.5 ml of dioxane is added. The mixture is heated with an oil bath (100° C.) and a solution of dinorbornylphosphine-{2-(N,N-dimethyl-2'-amino-biphenyl)-C,N}palladium-(II)chloride (5.6 mg, 0.01 mmols) in 0.5 ml of dioxane is added. After a reaction time of 1 hour, the yield is determined by GC and is 98.5% (GC).

Example B12

Reaction with 0.1 mol % of dinorbornylphosphine-{2-(N,N-dimethyl-2'-amino-biphenyl)-C,N}palladium(II)chloride as catalyst.

The reaction is carried out as in example B5, but with 0.001 mmols of dinorbornylphosphine-{2-(N,N-dimethyl-2'-amino-biphenyl)-C,N}palladium(II)chloride. Yield after 16 hours reaction time: 74% (GC).

Examples B13 to B19

Use of Different Palladium Complexes

Potassium phosphate (0.76 g, 3 mmols) is placed under argon, and a solution of phenyl boric acid (0.18 g, 1.5 mmols), 4.chloroanisole (0.14 g, 1 mmol) and water (90 mg, 12.5 mmols) in 2.5 ml of dioxane is added. The mixture is heated with an oil bath (100° C.), and a solution of the palladium compounds (0.01 mmols Pd) and the phosphine (0.015 mmols) is added. After a reaction time of 16 hours, the yield is determined by GC. The results are given in table 2.

TABLE 2

| Ex. | palladium compound | phosphine | 4-methoxy-biphenyl yield in % (GC) |
|---|---|---|---|
| B13 | Pd(OAc)$_2$ | dinorbornylphosphine | 97 |
| B14 | [Pd complex with biphenyl-NMe$_2$ and OAc ligand]$_2$ | dinorbornylphosphine | 100 |
| B15 | | di-t-butylphosphine | 94 |
| B16 | [Pd complex with benzyl-NMe$_2$ and OAc ligand]$_2$ | [dinorbornylphosphine structure, PH] | 31 |
| B17 | [Pd complex with N-methyl-2-aminopyridine and OAc ligand]$_2$ | dinorbornylphosphine | 90 |
| B18 | [Pd complex with N-methylacetamide and OAc ligand]$_2$ | [dinorbornylphosphine structure, PH] | 30 |
| B19 | [Pd complex with quinoline and OAc ligand]$_2$ | dinorbornylphosphine | 90 |

Example B20

Preparation of di-p-tolylamine 4-toluidine (535 mg, 5.5 mmols), Pd$_2$(dba)$_3$xCHCl$_3$ (26 mg, 25 μmols) and diadamantyl-phosphine (22.8 mg, 75 μmol) are placed under argon, and 4-bromotoluene (850 mg, 5 mmols) in 10 ml of toluene and Na tert.-butylate (495 mg, 5 mmols) are added. The reaction mixture is stirred in an oil bath of 105° C. for 21 hours and then cooled. The title compound is purified by flash chromatography. The pure yield is 74%.

Example B21

Preparation of 1,2-diphenyl ethanone Na tert.-butylate (720 mg, 7.5 mmols), Pd$_2$(dba)$_3$xCHCl$_3$ (10.5 mg, 0.1 mmols) and diadmantylphosphine (91 mg, 0.3 mmols) are placed under argon, and tetrahydrofuran (5 ml), bromobenzene (0.53 ml, 5 mmols) and acetophenone (1.75 ml, 15 mmols)

are added. The reaction mixture is stirred in an oil bath of 70° C. for 23 hours and then cooled. The yield according to NMR is 36%.

C) Examples for Variant b)

Example C1
Preparation of 3-trifluoromethyl-benzoic acid butyl ester

Palladium chloride [0.302 g (20%ige Pd solution), 0.35 mmols] and 1-diadamantylphosphine (0.836 g, 2.76 mmols) are stirred under argon for 10 minutes in 5 ml of n-butanol. This mixture is added to 3-bromobenzotrifluoride (8.0 g, 35 mmols), triethylamine (3.85 g, 38 mmols) and 20 ml of n-butanol in an autoclave. The autoclave is sealed and rinsed three times with nitrogen and carbon monoxide. 5.2 bars of carbon monoxide are applied, and the autoclave is heated for 4 days at 135° C. After cooling, filtration takes place and the solvent is distilled off. The raw product is purified by distillation (92° C. at 0.55 mbars). Yield of title compound: 5.8 g (70%).

Example C2
Preparation of 4-trifluoromethyl-benzoic acid butyl ester

Sodium carbonate (2.22 g, 21 mmols), 4-bromobenzotrifluoride (3.15 g, 14 mmols) and 26 ml of n-butanol are placed in a glass autoclave. The autoclave is rinsed with nitrogen and heated to 120° C. A solution of palladium bis(benzonitrile) dichloride (54 mg, 0.14 mmols) and dinorbornylphosphine (0.22 g, 0.98 mmols) in 2 ml of n-butanol (prepared under argon) is added, and then 1 bar CO is applied. After 16 hours at 130° C., the mixture is allowed to cool. The reaction mixture is taken up in water and methylene chloride. The organic phase is separated, dried and concentrated. The residue is purified by bulb tube distillation. Yield of title compound: 1.7 g (49%).

Example C3
Preparation of 4-trifluoromethyl-benzoic acid butyl ester from 4-chlorobenzotrifluoride Sodium carbonate (2.43 g, 23 mmols), 4-chlorobenzotrifluoride (2.8 g, 21 mmols) and 40 ml of n-butanol are placed in a glass autoclave. The autoclave is rinsed with nitrogen and heated to 120° C. A solution of palladium bis(benzonitrile) dichloride (161 mg, 0.42 mmols) and dinorbornylphosphine (420 mg, 1.90 mmols) in 2 ml of n-butanol (prepared under argon) is added, and then 5 bars CO are applied. After 16 hours at 145° C., the mixture is allowed to cool. The reaction mixture is taken up in water and tert.-butylmethyl ether. The organic phase is analysed by GC. GC yield of title compound: 18% (percent per unit area).

Example C4
Preparation of 2-pyridine-carboxylic acid

Sodium carbonate (3.34 g, 32 mmols), 2-chloropyridine (2.38 g, 21 mmols) and 40 ml of ethanol are placed in a glass autoclave. The autoclave is rinsed with nitrogen and heated to 100° C. A solution of palladium bis(benzonitrile) dichloride (161 mg, 0.42 mmols) and dinorbornylphosphine (420 mg, 1.90 mmols) in 2 ml of ethanol (prepared under argon) is added, and then 5 bars CO are applied. After 16 hours at 120° C., the mixture is allowed to cool. The reaction mixture is taken up in water and methylene chloride. The aqueous phase is separated, acidified with concentrated hydrochloric acid and concentrated. The residue is extracted with ethanol and, after filtration, the ethanol is distilled off in a vacuum. The solid is recrystallised from water/ethanol/acetone. Yield of title compound as the hydrochloride: 2.13 g (64%).

Example C5
Preparation of 2-fluorobenzoic Acid

Sodium carbonat (3.34 g, 32 mmols), 1-bromo-2-fluorobenzene (3.68 g, 21 mmols), water (1.1 g, 63 mmol) and 40 ml of dioxane are placed in a glass autoclave. The autoclave is rinsed with nitrogen and heated to 120° C. A solution of palladium bis(benzonitrile) dichloride (161 mg, 0.42 mmols) and dinorbornylphosphine (420 mg, 1.90 mmols) in 2 ml of dioxane (prepared under argon) is added, and then 6 bars CO are applied. After 16 hours at 135° C., the mixture is allowed to cool. The reaction mixture is taken up in sodium hydroxide solution and diethyl ether. The aqueous phase is separated and acidified with concentrated hydrochloric acid. The title compound precipitates in the form of colourless crystals. Yield of title compound: 1.6 g (54%).

Example C6
Preparation of (N,N-dimethyl-4-amino-benzoyl)morpholine

Morpholine (2.74 g, 32 mmols), 4-bromo-N,N-dimethylaniline (4.2 g, 21 mmols) and 40 ml of dioxane are placed in a glass autoclave. The autoclave is rinsed with nitrogen and heated to 110° C. A solution of palladium bis(benzonitrile) dichloride (161 mg, 0.42 mmols) and dinorbornylphosphine (420 mg, 1.90 mmols) in 2 ml of dioxane (prepared under argon) is added, and then 6 bars CO are applied. After 16 hours at 135° C., the mixture is allowed to cool. The solvent is distilled off in a vacuum, and the crude product is purified by chromatography (ethyl acetate: Rf=0.43). Yield of title compound: 2.06 g (42%).

D) Examples for Variant c)

Example D1
Preparation of 4-trifluoromethyl-cinnamic Acid Butyl Ester 4-chlorobenzotrifluoride (0.71 g, 5 mmols), acrylic acid butyl ester (0.97 g, 7.6 mmols), sodium carbonate (0.81 g, 7.6 mmols), tetrabutylammonium bromide (161 mg, 0.5 mmol) and 4 ml DMA are placed under argon in a reaction flask and heated to 130° C. Afterwards, 22 mg of dinorbornyl phosphine in 1 ml of DMA and 0.2 ml of a 0.25 M PdCl$_2$ solution in DMA are dispensed in after one another. The reaction mixture is stirred for 10 hours at 130° C. and then cooled. The yield determined in the reaction mixture by gas chromatography is 95% (GC).

Example D2
Reactions of Different Chloro-Aromatics with Acrylic Acid Butyl Ester Sodium carbonate (0.81 g; 7.6 mmols) and diadamantyl phosphine (60.6 mg, 0.2 mmols) are placed under argon. Afterwards, gassed dimethyl acetamide (4 ml), the chloro-aromatics (5 mmols) and the acrylic acid butyl ester (0.70 g, 0.87 ml, 5.5 mmols) are added. The reaction mixture is heated with an oil bath (140° C.), and after 5 minutes, the palladium dichloride solution (0.4 ml of a 0.25 M solution in DMA) is added. The reaction mixture is stirred for 14 hours at 140° C. After cooling, the reaction mixture is extracted with diethyl ether and water. The organic phase is dried (sodium sulfate) and concentrated in a vacuum. The residue is purified by column chromatography over silica gel. The results are given in table 3.

TABLE 3

Heck reactions with different chloro-aromatics in the presence of
palladium chloride and diadamantyl phosphine.

| Educt | product | cat. amount | conversion according to GC[b] | isolated yield |
|---|---|---|---|---|
| chlorobenzene | cinnamic acid butyl ester | 2 | 98 | 75 |
| 4-chloroanisole | 4-methoxy-cinnamic acid butyl ester | 2 | 89 | 71[a] |
| 4-chlorotoluene | 4-methyl-cinnamic acid butyl ester | 2 | 93 | 87 |
| 4-chlorobenzotrifluoride | 4-trifluoromethyl-cinnamic acid butyl ester | 2 | 80 | 76 |
| 4-chloroacetophenone | 4-acetyl-cinnamic acid butyl ester | 2 | 100 | 60 |
| 4-chlorobenzaldehyde | 4-formyl-cinnamic acid butyl ester | 2 | 100 | 71 |
| 4-chloronitrobenzene | 4-nitro-cinnamic acid butyl ester | 2 | 100 | 82 |
| 3-chlorodimethylaniline | N,N-dimethyl-3-amino-cinnamic acid butyl ester | 2 | 100 | 90 |
| 3-chlorobenzoic acid ethyl ester | 3-ethyloxycarbonyl-cinnamic acid butyl ester | 2 | 100 | 55 |
| 2-chlorobenzonitrile | 2-cyano-cinnamic acid butyl ester | 4 | 84 | 50 |
| 1-chloro-2,4-difluoro-benzene | 2,4-difluoro-cinnamic acid butyl ester | 4 | 65 | 27 |
| 1-chloronaphthalene | 3-(1-naphthyl)-acrylic acid butyl ester | 2 | 57 | 38 |
| 2-chloropyridine | 3-(2-pyridyl)-acrylic acid butyl ester | 4 | 53 | 10 |
| 3-chloropyridine | 3-(3-pyridyl)-acrylic acid butyl ester | 2 | 100 | 84 |
| 2-chlorothiophene | 3-(2-thiophenyl)-acrylic acid butyl ester | 2 | 87 | 15 |
| β-bromostyrene | 5-phenyl-butadiene-carboxylic acid butyl ester | 2 | 100 | 50 |

[a]purified by bulb tube distillation.
[b]conversion = 100 - percent per unit area of educt/sum of percentages per unit area of product, by-product and educt.

Example D3
Reaction of 4-chlorotoluene with Vinyl Butyl Ether

Potassium acetate (0.75 g; 7.6 mmols) and diadamantyl phosphine (121 mg, 0.4 mmols) are placed under argon. Afterwards, argon-gassed dimethyl acetamide (4 ml), 4-chlorotoluene (0.59 ml, 5 mmols) and acrylic acid butyl ester (0.70 g, 5.5 mmols) are added. The reaction mixture is heated with an oil bath (140° C.), and a palladium dichloride solution (0.8 ml of a 0.25 M solution in DMA) is added. The reaction mixture is stirred for 19 hours at 140° C. After cooling, the reaction mixture is extracted with ether and water. The organic phase is dried (sodium sulfate) and concentrated in a vacuum. The residue is purified by chromatography on silica gel. Yield of 1-butoxy-2-(p-tolyl)-ethylene: 0.45 g (47%). In addition, 0.13 g (19%) of methyl tolyl ketone are isolated.

Example D4
Heck Reaction of 4-chlorotoluene with Styrene

Sodium carbonate (0.81 g, 7.6 mmols) and diadamantyl phosphine (60.6 mg, 0.2 mmols) are placed under argon. Afterwards, gassed dimethyl acetamide (4 ml), 4-chlorotoluene (0.59 ml, 5 mmols) and styrene (0.57 g, 5.5 mmols) are added. The reaction mixture is heated with an oil bath (140° C.), and after 5 minutes, the palladium dichloride solution (0.4 ml of a 0.25 M solution in DMA) is added. The reaction mixture is stirred for 18 hours at 140° C. After cooling, the reaction mixture is extracted with tert.-butyl methyl ether and water. The organic phase is dried (sodium sulfate) and concentrated in a vacuum. The residue is purified by chromatography on silica gel. Yield of 4-methyl-stilbene: 0.77 g (79%).

Example D5
Heck Reaction of 4-chlorotoluene with ethylene

Sodium carbonat (8.1 g, 76 mmols), diadamantyl phosphine (606 mg, 2 mmols), hydro-quinone monomethyl ether (67 mg), dimethylacetamide (40 ml), 4-chlorotoluene (6.3 g, 50 mmols) and palladium dichloride solution (1.0 mmols in 4.0 ml DMA) are placed under nitrogen in an autoclave. 30 bars ethylene are applied, and the reaction mixture is heated at 135° C. for 20 hours. After cooling, the reaction mixture is extracted with diethyl ether and water. The organic phase is dried (sodium sulfate) and concentrated in a vacuum. The residue is purified by distillation. Yield of 4-methyl-styrene (80° C. at 70 mbars): 2.7 g (46%).

Example D6
Heck Reactions with 4-chloroanisole and Acrylic Acid Butyl Ester with Different Phosphines Sodium carbonate (0.81 g, 7.6 mmols) is placed under argon. Afterwards, gassed dimethylacetamide (3 ml), 4-chloroanisole (0.61 ml, 5 mmols), acrylic acid butyl ester (1.2 ml, 7.6 mmols), diethylene glycol dibutyl ether (100 mg, internal standard), ligand (0.1 mmols in 1.0 ml DMA) and palladium dichloride (0.2 ml of a 0.25 M solution in DMA) are added. The reaction mixture is heated for 19 hours by an oil bath (140° C.). The yields are determined by GC using the internal standard. The results are given in table 4.

TABLE 4

| phosphine | 4-methoxy-cinnamic acid butyl ester yield in % (GC) |
|---|---|
| dicyclohexyl phosphine | 50 |
| dinorbornylphosphine | 70 |
| diadamantyl phosphine | 77 |
| di-t-butylphosphine | 82 |
| 4,8-dimethyl-2-phosphabicyclo(3,3,1)nonane | 47 |
| 1-phospha-3,5-dioxa-2,4,6-triisopropylcyclohexane | 64 |

Example D7
Heck Reactions with 4-chloroanisole and Acrylic Acid Butyl Ester with Different Palladium Compounds Sodium carbonate (0.81 g, 7.6 mmols) and palladium compounds (0.025 mmols Pd) are placed under argon. Afterwards, gassed dimethylacetamide (3 ml), 4-chloroanisole (0.61 ml, 5 mmols), acrylic acid butyl ester (1.2 ml, 7.6 mmols), diethylene glycol dibutyl ether (100 mg, internal standard), and diadamantyl phosphine (0.05 mmols in 0.5 ml DMA) are added. The reaction mixture is heated for 19 hours by an oil bath (140° C.). The yields are determined by GC using the internal standard. The results are given in table 5.

TABLE 5

| palladium complex | 4-methoxy-cinnamic acid butyl ester yield in % (GC) |
| --- | --- |
| Pd(OAc)$_2$ | 52 |
| PdCl$_2$ | 60 |
| Pd(dba)$_3$*CHCl$_3$ | 35 |
| 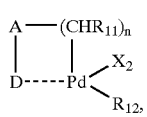 | 61 |
| (structure with NMe$_2$) | 65 |
| (structure with CH$_2$NMe$_2$) | 59 |
| (structure with N-methylpyridyl) | 66 |
| (structure with CH$_2$-pyridyl) | 74 |
| (structure with N-C(O)Me) | |

TABLE 5-continued

| palladium complex | 4-methoxy-cinnamic acid butyl ester yield in % (GC) |
| --- | --- |
|  | 55 |

What we claim is:

1. A compound of formula VIII, $$A\!\!-\!\!(CHR_{11})_n$$
$$|\qquad\qquad|$$
$$D\!-\!-\!-\!-\!Pd\!\!<\!\!\begin{array}{l}X_2\\R_{12},\end{array}$$
(VIII)

wherein
A signifies a bivalent aromatic hydrocarbon radical;
D represents a substituent which contains atoms coordinating with palladium, and D is bonded to radical A in ortho position to the group —CHR$_{11}$—;
X$_2$ is the anion of a monobasic inorganic acid or organic acid;
n is 0 or 1;
R$_{11}$ signifies hydrogen or C$_1$–C$_4$-alkyl;
R$_{12}$ represents a secondary monophosphine with aliphatic, branched or cyclic substituents; and
A and D, together with the group —CHR$_{11}$— and the palladium atom, form a 4- to 6-membered ring.

2. A compound according to claim 1, wherein the coordinating atoms in substituent D are O, S, N and P.

3. A compound according to claim 1, wherein R$_{12}$ is a secondary monophosphine of formula I

HPR$_1$R$_2$ (I), wherein R$_1$ and R$_2$, independently of one another, signify α-branched alkyl or cycloalkyl, or R$_1$ and R$_2$, together with the P-atom, represent a P-heterocycloaliphatic radical with a total of 4 to 8 ring members.

4. A compound according to claim 1, wherein A contains 5 to 18 carbon atoms.

5. A compound according to claim 1, wherein substituent D comprises: azo and imino groups of formulae —N=N—R$_{13}$ and —CH$_2$—N=N—R$_{13}$, —(R$_{14}$)CH=N—R$_{13}$, —N=CH—R$_{13}$ and —CH$_2$—N=CH—R$_{14}$; those of formula —NH—C(R$_{14}$)=NR$_{13}$; those of formula —X$_4$—CH$_2$—X$_5$—R$_{15}$, wherein X$_4$ signifies —O—, —S— or —NR$_{16}$—, R$_{15}$ is H or C$_1$–C$_4$-alkyl, and R$_{16}$ signifies H or C$_1$–C$_4$-alkyl; those of formulae (R$_{14}$)C(O)—NR$_{13}$—, those of formulae —CH=N—OR$_{13}$ or —CH=N—N(R$_{13}$)$_2$; and aliphatic heterocycles, which contain in the ring a group —NR$_{13}$— or —PR$_{13}$— in α-position to the bond; whereby R$_{13}$ signifies C$_1$–C$_4$-alkyl, phenyl, cyclohexyl or benzyl, and R$_{14}$ is H, C$_1$–C$_8$-alkyl, C$_5$–C$_6$-cycloalkyl, C$_6$–C$_{10}$-aryl or C$_6$–C$_{12}$-aralkyl.

6. A compound according to claim 1, wherein substituent D corresponds to a formula

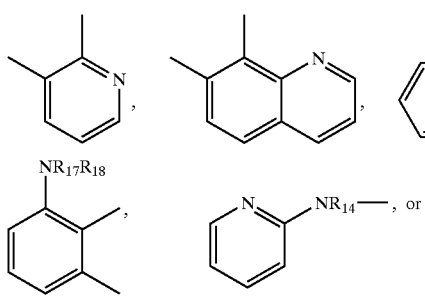
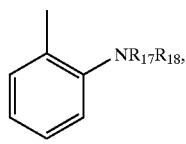
wherein $R_{14}$ is H, $C_1$–$C_8$-alkyl, $C_5$–$C_6$-cycloalkyl, $C_6$–$C_{10}$-aryl or $C_6$–$C_{12}$-aralkyl, $R_{17}$ and $R_{18}$ independently signify $C_1$–$C_4$-alkyl, phenyl, cyclohexyl or benzyl, and when D corresponds to one of the above bivalent formulae, then D in 1,2-position is condensed to A.
* * * * *